(12) United States Patent
Wang et al.

(10) Patent No.: US 9,107,905 B2
(45) Date of Patent: Aug. 18, 2015

(54) **MODULATORS OF *CANDIDA* HYPHAL MORPHOGENESIS AND USES THEREOF**

(71) Applicant: Agency for Science, Technology and Research, Connexis (SG)

(72) Inventors: Yue Wang, Singapore (SG); Xiao-Li Xu, Singapore (SG); Raymond Teck Ho Lee, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 181 days.

(21) Appl. No.: 13/747,413

(22) Filed: Jan. 22, 2013

(65) Prior Publication Data

US 2013/0196367 A1  Aug. 1, 2013

Related U.S. Application Data

(62) Division of application No. 12/438,761, filed as application No. PCT/SG2007/000265 on Aug. 21, 2007, now Pat. No. 8,383,110.

(60) Provisional application No. 60/823,636, filed on Aug. 25, 2006.

(51) Int. Cl.
*C07K 16/44* (2006.01)
*C12Q 1/02* (2006.01)
*A61K 39/395* (2006.01)

(52) U.S. Cl.
CPC .............. *A61K 39/395* (2013.01); *C07K 16/44* (2013.01); *C12Q 1/02* (2013.01)

(58) Field of Classification Search
CPC .... C07K 14/37; C07K 14/40; C07K 14/4702; C07K 2317/76; A61K 36/06; A61K 39/00
See application file for complete search history.

(56) References Cited

U.S. PATENT DOCUMENTS

| 4,396,607 A | 8/1983 | Lefrancier et al. |
| 4,522,811 A | 6/1985 | Eppstein et al. |
| 8,383,110 B2 | 2/2013 | Wang et al. |
| 8,889,134 B2 | 11/2014 | Wang et al. |
| 2004/0203090 A1 | 10/2004 | Slesarev et al. |
| 2006/0241025 A1 | 10/2006 | Slesarev et al. |
| 2009/0258015 A1* | 10/2009 | Wang et al. ............... 424/133.1 |
| 2010/0215708 A1* | 8/2010 | Zumbuehl et al. ........... 424/422 |
| 2013/0195853 A1* | 8/2013 | Wang et al. ............... 424/133.1 |
| 2013/0196367 A1* | 8/2013 | Wang et al. ................... 435/34 |
| 2013/0252964 A1* | 9/2013 | Scott et al. .............. 514/252.11 |

FOREIGN PATENT DOCUMENTS

| EP | 0680974 A1 | 11/1995 |
| WO | WO-2004/091552 A2 | 10/2004 |
| WO | WO-2008/024075 A1 | 2/2008 |

OTHER PUBLICATIONS

International Search Report and Written Opinion mailed Oct. 12, 2007 in connection with PCT/SG2007/000265.
International Preliminary Report on Patentability dated Jul. 15, 2008 in connection with PCT/SG2007/000265.
Extended European Search Report mailed Feb. 7, 2011 in connection with EP07794275.3.
Ernst, Transcription factors in *Candida albicans*—environmental control of morphogenesis. Microbiology. Aug. 2000;146 ( Pt 8):1763-74.
Ogawa et al., Enhancement of serum antibody production in mice by oral administration of lipophilic derivatives of muramylpeptides and bacterial lipopolysaccharides with bovine serum albumin. Methods Find Exp Clin Pharmacol. Jan. 1986;8(1):19-26.
Shimi et al., 4,4'-isopropylidine-bis(2-isopropyl)phenol, a new inhibitor for cell wall formation of *Bacillus subtilis*. Antimicrob Agents Chemother. Apr. 1976;9(4):580-4.
Wang et al., Bacterial peptidoglycan-derived molecules activate *Candida albicans* hyphal growth. Commun Integr Biol. Oct.-Dec. 2008;1(2):137-9.
Xu et al., Bacterial peptidoglycan triggers *Candida albicans* hyphal growth by directly activating the adenylyl cyclase Cyr1p. Cell Host Microbe. Jul. 17, 2008;4(1):28-39.
Cassola et al., *Candida albicans* lacking the gene encoding the regulatory subunit of protein kinase A displays a defect in hyphal formation and an altered localization of the catalytic subunit. Eukaryot Cell. Feb. 2004;3(1):190-9.
Rocha et al., Signaling through adenylyl cyclase is essential for hyphal growth and virulence in the pathogenic fungus *Candida albicans*. Mol Biol Cell. Nov. 2001;12(11):3631-43.

\* cited by examiner

*Primary Examiner* — Nita M Minnifield
(74) *Attorney, Agent, or Firm* — Wolf, Greenfield & Sacks, P.C.

(57) ABSTRACT

The invention relates to modulation of fungal morphology between yeast-to-hyphal growth transition by controlling muramyl-L-alanine concentration and uses thereof.

4 Claims, 5 Drawing Sheets

Hyphin (dAcMDP)                    D-Ala-L-isoGln

MODULATORS OF *CANDIDA* HYPHAL MORPHOGENESIS AND USES THEREOF

RELATED APPLICATIONS

This application is a divisional of U.S. application Ser. No. 12/438,761, filed on Feb. 25, 2009, now U.S. Pat. No. 8,383,110, which is a national stage filing under 35 U.S.C. §371 of International application number PCT/SG2007/000265, filed Aug. 21, 2007, and which claims priority under 35 U.S.C. §119 from U.S. provisional application Ser. No. 60/823,636, filed Aug. 25, 2006, the entire contents of each of which are incorporated by reference herein.

FIELD OF THE INVENTION

The invention relates to modulation of fungal morphology between yeast-to-hyphal growth transition and use thereof.

BACKGROUND ART

*Candida albicans* is the most prevalent fungal pathogen in humans, causing life threatening systemic infections in immuno-compromised patients. Largely due to the rampant AIDS pandemic of the past quarter of a century the fungus *C. albicans* has rapidly risen from a largely harmless commensal of the humans to the most prevalent fungal pathogen (Odds, F. C. (1985) *Crit. Rev. Microbiol.* 12, 45-93; Calderone, R. A., and Fonzi, W. A. (2001) *Trends Microbiol.* 9, 327-935; Berman, J., and Sudbery P. E. (2002) *Nat. Rev. Genet.* 3, 918-930; Gow, N. A., et al (2002) *Curr. Opin. Microbial.* 5, 366-371; Liu, H. (2002) *Int. J. Med. Microbial.* 292, 299-311). *C. albicans* commonly causes life-threatening systemic infections in immuno-compromised patients. A well established virulence trait of *C. albicans* is its ability to switch between several morphological forms such as budding yeast, pseudohyphae and true hyphae in response to environmental cues (Leberer, E., et al (1996) *Proc. Natl. Acad. Sci. USA* 93, 13217-13222; Lo, H. J., et al (1997) *Cell* 90; 939-949; Zheng, X., et al (2004) *EMBO J.* 23, 1845-1856.). Serum is an inducer of this switch.

The yeast-hypha switch is well documented to play important roles in penetrating host tissues and escaping from phagocytic destruction (Cutler, J. E. (1991) *Annu. Rev. Microbiol.* 45, 187-218; Lo, H. J., et al (1997) *Cell* 90; 939-949; Phan, Q. T., et al (2000) *Infect. Immun.* 68, 3485-3490; Bal, C., et al (2002). *Mol. Microbiol.* 45, 31-44), two processes generally important for pathogenesis and virulence of many microbial pathogens. Indeed, *C. albicans* mutants defective in the yeast-hypha transition exhibit significantly reduced virulence (Leberer, E., et al (1997) *Curr. Biol.* 7, 539-546; Lo, H. J., et al (1997) *Cell* 90; 939-949; Braun, B. R., and Johnson, A. D. (1997). *Science* 277, 105-109; Calderone, R. A., and Fonzi, W. A. (2001). *Trends Microbiol.* 9, 327-935; Stoldt, V. R., et al (1997) *EMBO J.* 16, 1982-1991; Zheng, X., et al (2004) *EMBO J.* 23, 1845-1856). Thus, blocking the morphological switch holds high promise for developing effective medical interventions for candidal infections. Although a variety of inducers have been reported to trigger the yeast-hypha switch under laboratory conditions, serum is undisputedly the most potent and physiologically relevant (Gow NA. (1997) *Curr. TOP. Med. Mycol.* 8, 4355; Ernst, J. F. (2000) *Microbiology* 146, 1763-1774). In spite of the fact that the serum activity was first reported half a century ago (Reynolds, R., and Braude, A. I. (1956) *Olin. Res. Proc* 4, 40), the identity of the inducer(s) and its sensor in *C. albicans* remain ill defined.

Feng et al. (1999) first found that the majority of the serum hyphal inducer(s) can pass through a dialysis membrane with a molecular weight cut-off of 1 kDa (Feng, Q. et al (1999). *J. Bacterial.* 181, 6339-6346.). Hudson et al. (2004) recently reported that there are two distinct hyphal inducers in serum (Hudson, D. A., et al (2004) *Microbiology* 150, 3041-3049). Glucose was described to be a dialyzable inducer responsible for ~80% of the inducing activity. A minor inducer was found to be non-dialyzable and trichloroacetic acid-precipitable. This report observed that adding the dialyzable fraction to glucose-containing medium did not induce the yeast-hypha switch.

The key signalling cascade responsible for serum-induced hyphal growth has been well established to be the cyclic AMP/protein kinase A (PKA) pathway (Leberer, E., et al (2001) *Mol. Microbiol.* 42, 673-687; Liu, H. (2001) *Curr. Opin. Microbiol.* 4, 728-735; Roche, C. R., et al (2001) *Mol. Biol. Cell* 12, 3631-3643). *C. albicans* genome contains a single adenylate cyclases gene CDC35. Hyphal induction activates this enzyme, resulting in a spike of cellular cAMP level and subsequent activation of PKA (Bahn, Y. S, and Sundstrom, P. (2001) *J. Bacteriol.* 183, 3211-3221; Roche, C. R., et al (2001) *Mol. Biol. Cell* 12, 3631-3643). This pathway leads to the activation of a transcription factor CaEfg1p which regulates the expression of a large number of hypha-specific genes (Ernst, J. F. (2000) *Microbiology* 146, 1763-1774; Lane, S., et al (2001) *J. Biol. Chem.* 276, 48988-48996; Liu, H. (2001) *Curr. Opin. Microbiol.* 4, 728-735). CDC35 deletion causes a complete loss of hyphal development as well as severely retarded yeast growth (Roche, C. R., et al (2001) *Mol. Biol. Cell* 12, 3631-3643). Although Cdc35 is thought to reside near the very beginning of the cAMP/PKA pathway, its possible role in signal sensing has not been addressed.

Cdc35 contains at least three functional domains: an N-terminal RAS-association (RA) domain, a middle domain made up of 15 LRRs and a carboxy terminal catalytic domain of adenylyl cyclase. The long LRR domain is a prominent feature of several families of proteins involved in the innate immunity in mammals, insects and plants that have evolved to recognize, a range of conserved pathogen associated molecular patterns including peptidoglycans (PG), lipopolyssacharides, lipoproteins, etc (Chamaillard, M., et al (2003). *Cell Microbiol.* 5, 581 592; Chamaillard, M., (2003) *Nat. Rev. Immunol.* 4, 702-707; Inohara, N., and Nunez, G. (2003). *Nat. Rev. Immunol.* 3, 371-382; Girardin, S. E., and Philpott; D. J. (2004) *Eur. J. Immunol.* 34, 1777-1782).

The present invention seeks to provide a hitherto unknown means for modulating hyphal growth. It provides methods for screening modulators that are capable of achieving this outcome as well as therapeutically active compounds that are able to interfere with *C. albicans* virulence.

GENERAL

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

SUMMARY OF THE INVENTION

The present invention is derived from the discovery that muramyl-L-alanine and compounds that include muramyl-L-alanine in their core structure such as bacterial peptidoglycan compounds like muramyl-L-alanine, muramyl-L-alanyl-D-isoglutamine, N-acetyl-muramyl-L-alanine, and N-acetyl-muramyl-L-alanyl-D-isoglutamine, constitute the principal *Candida* hyphal inducers in body fluids. These compounds bind with specific affinity within the leucine-rich-repeats (LRR) domain of CaCdc35p; an essential upstream regulator for hyphal growth in *Candida* (eg. *Candida albicans*). Furthermore, LRR domain mutations induced in CaCdc35p abolished (a) the binding of muramyl-L-alanine and compounds that include muramyl-L-alanine in their core structure, and (b) hyphal growth.

Thus, the invention provides a method for treating a patient to at least affect *Candida* hyphal growth, which comprises the step of: contacting the infection with (a) an antagonist to muramyl-L-alanine and/or compounds that include muramyl-L-alanine in their core structure and/or (b) a compound that engages the LRR domain of CaCdc35p preventing muramyl-L-alanine and/or compounds that include muramyl-L-alanine in their core structure from binding to the LRR domain. Preferably, the antagonist interferes with *Candida* hyphal growth by means that remove, degrade, neutralize or compete with muramyl-dipeptide related compounds in a patient's body fluids (such as without limitation, blood, plasma, bodily fluids in esophagus, throat, interstitial fluid, lymph, mucus, etc). More preferably, the antagonist is effective against muramyl-L-alanyl-D-isoglutamine, N-acetylmuramyl-L-alanine, N-acetylmuramyl-L-alanyl-D-isoglutamine or muramyl-L-alanyl-L-isoglutamine. In a highly preferred form, the antagonist is specifically effective against muramyl-L-alanyl-D-isoglutamine.

An alternative form of the present invention resides in muramyl-L-alanine and/or compounds that include muramyl-L-alanine in their core structure in the manufacture of a medicament for treating a patient infected with *Candida*, preferably a medicament used in treatment to affect *candida* hyphal growth.

The present invention also relates to compositions including pharmaceutical compositions comprising a therapeutically effective amount of (a) an antagonist to muramyl-L-alanine and/or compounds that include muramyl-L-alanine in their core structure and/or (b) a compound that engages the LRR domain of CaCdc35p preventing muramyl-L-alanine and/or compounds that include muramyl-L-alanine in their core structure from binding to the LRR domain. As used herein a compound will be therapeutically effective if it is able to affect *Candida* hyphal growth. The compound may further comprise an adjuvant capable of inducing an immune response in a patient.

The invention also provides a means for prognosing or diagnosing the course of a *Candida* infection, comprising the steps of: measuring the amount of muramyl-L-alanine and/or compounds that include muramyl-L-alanine in their core structure in body fluids sampled from a *Candida* infection.

Further the invention provides a means for determining the most effective treatment for a *Candida* infection, comprising the steps of: diagnosing the state of hyphal growth according to the above method and then determining the patient's treatment according to whether hyphal growth is expected or not.

Consistent with the invention there is provided a means for screening for agonists and antagonists of *Candida* hyphal growth comprising the steps of: (a) contacting (i) muramyl-L-alanine and/or compounds that include muramyl-L-alanine in their core structure and (ii) the LRR domain of CaCdc35p from a *Candida* species with a sample compound, and (b) detecting whether the sample compound exhibits agonistic or antagonistic activity towards the interaction. Preferably, the method is used to screen for antagonistic drugs that are capable of interfering either in a direct or indirect manner with the interaction between *C. albicans* (such as, muramyl-L-alanine, muramyl-L-alanyl-D-isoglutamine, N-acetyl-muramyl-L-alanine, N-acetyl-muramyl-L-alanyl-D-isoglutamine, muramyl-L-alanyl-L-isoglutamine).

The present invention also relates to compounds identified by the above method and their use in treating *Candida* hyphal growth in a patient.

In another aspect of the invention a method of modulating morphogenesis of a fungus by controlling the concentration of muramyl-L-alanine in the fungal environment. The fungal environment may include body fluids (such as without limitation, blood, plasma, bodily fluids in esophagus, throat, interstitial fluid, lymph, mucus, etc). The fungus may be a yeast such as *Candida* or *Candida albicans*. The modulation may include inducing hyphal morphogenisis by increasing the concentration of muramyl-L-alanine or inhibit the hyphal morphogenisis by removing degrading or neutralising the concentration of muramyl-L-alanine. The concentration of muramyl-L-alanine may be removed degraded or neutralised by an antibody such as a catalytic antibody.

Accordingly, the methods described herein may be used in prognostic, diagnostic, therapeutic and drug screening methods. Other aspects and advantages of the invention will become apparent to those skilled in the art from a review of the ensuing description, which proceeds with reference to the following illustrative drawings.

DETAILED DISCLOSURE OF THE INVENTION

Figure 1:
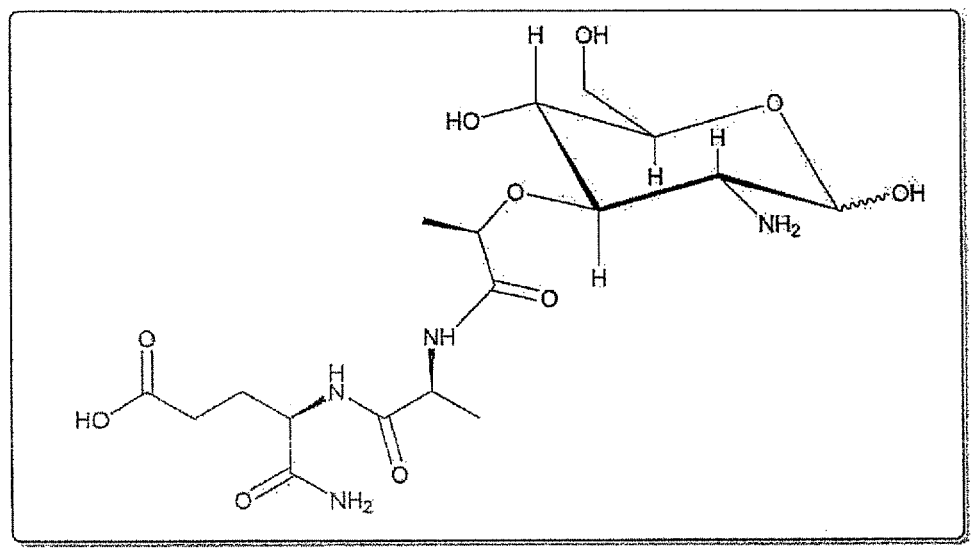
FIG. 1: Chemical structures of hyphin a muramyl-L-alanine that does not have the N-acetyl group commonly found in bacterial PGNs and muramyl-L-alanyl-D-isoglutamine.
Figure 1:
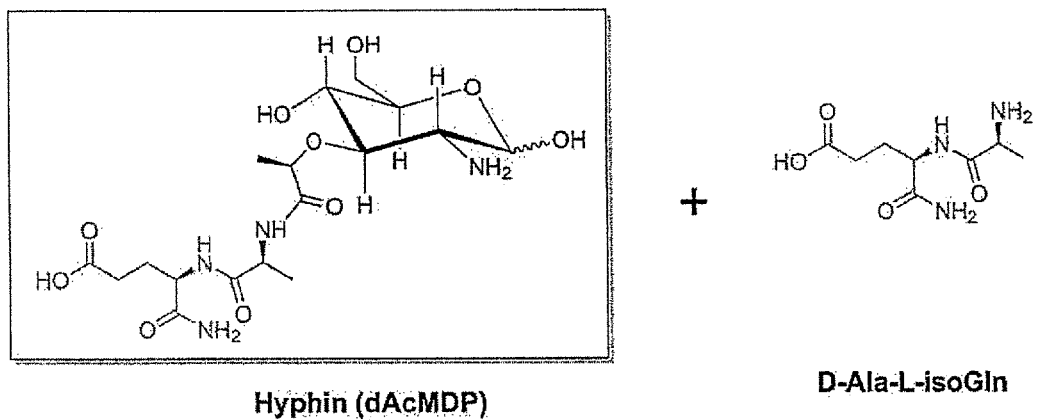

The present invention derives from the applicant's discovery that muramyl-L-alanyl-D-isoglutamine is approximately 300 times more active than N-acetylglucosamine as an inducer of *Candida* hyphal growth. N-acetylglucosamine is currently the most potent single-compound hyphal inducer known. Further, this research has also revealed that muramyl-L-alanine-D-isoglutamine binds with high affinity within the LRR domain of CaCdc35p and that LRR-domain mutations induced in CaCdc35p abolished muramyl-L-alanyl-D-isoglutamine binding and hyphal growth. These data suggest that CaCdc35p plays a role in signal recognition as well as signal transduction. These data reveal that CaCdc35p plays central a role in signal recognition as well as signal transduction. These findings unveil an important human pathogenic factor for *Candida* infection and the use of an evolutionarily conserved mechanism in this pathogen-host interaction.

Method for Treating a Patient with a *Candida* Infection

On the basis of the above, the present invention provides a method for treating a patient with a *Candida* infection or an infection from a related organism, which comprises the step of: contacting the infection with (a) an antagonist to muramyl-L-alanine and/or compounds that include muramyl-L-alanine in their core structure and/or (b) a compound that engages the LRR domain of CaCdc35p preventing muramyl-L-alanine and/or compounds that include muramyl-L-alanine in their core structure from binding to the LRR domain. Desirably, the antagonist is provided in a therapeutic effective amount.

An alternative form of the present invention resides in muramyl-L-alanine and/or compounds that include muramyl-L-alanine in their core structure in the manufacture of a medicament for treating a patient infected with *Candida*, preferably a medicament used in treatment to affect *candida* hyphal growth.

"Treatment" and "treat" and synonyms thereof refer to both therapeutic treatment and prophylactic or preventative measures, wherein the object is to prevent or slow down (lessen) a *Candida* condition, in particular *Candida* Hyphal growth. Those in need of such treatment include those already with a *Candida* infection as well as those prone to getting it or those in whom a *Candida* infection is to be prevented.

As used herein a "therapeutically effective amount" of a compound will be an amount of active agent that is capable of preventing or at least slowing down (lessening) a *Candida* condition, in particular *Candida* hyphal growth. Dosages and administration of an antagonist of the invention in a pharmaceutical composition may be determined by one of ordinary skill in the art of clinical pharmacology or pharmacokinetics. See, for example, Mordenti and Rescigno, (1992) *Pharmaceutical Research,* 9:17-25; Morenti et al., (1991) *Pharmaceutical Research,* 8:1351-1359; and Mordenti and Chappell, "The use of interspecies scaling in toxicokinetics" in Toxicokinetics and New Drug Development, Yacobi et al. (eds) (Pergamon Press: NY, 1989), pp. 42-96. An effective amount of the antagonist to be employed therapeutically will depend, for example, upon the therapeutic objectives, the route of administration, and the condition of the mammal. Accordingly, it will be necessary for the therapist to titer the dosage and modify the route of administration as required to obtain the optimal therapeutic effect. A typical daily dosage might range from about 10 ng/kg to up to 100 mg/kg of the mammal's body weight or more per day, preferably about 1 μg/kg/day to 10 mg/kg/day.

Preferably, the antagonist interferes with *Candida* hyphal growth by means that affect the concentration or presence of or binding activity of muramyl-dipeptide-related compounds in body fluids (such as without limitation, blood, plasma, bodily fluids in esophagus, throat, interstitial fluid, lymph, mucus, etc) to the LRR-domain in CaCdc35p. More preferably, the antagonist is effective against muramyl-L-alanyl-D-isoglutamine, N-acetylmuramyl-L-alanine, N-acetylmuramyl-L-alanyl-D-isoglutamine or muramyl-L-alanyl-L-isoglutamine. In a highly preferred form, the antagonist is specifically effective against muramyl-L-alanyl-D-isoglutamine.

The term "antagonist" is used in the broadest sense, and includes any molecule that partially or fully blocks, inhibits, or neutralizes a biological activity of muramyl-L-alanine and/or compounds that include muramyl-L-alanine in their core structure. Such antagonists may work by engaging either muramyl-L-alanine and/or compounds that include muramyl-L-alanine in their core structure or they may engage the LRR domain of CaCdc35p preventing muramyl-L-alanine and/or compounds that include muramyl-L-alanine in their core structure from binding to the LRR domain.

Suitable antagonist molecules specifically include antagonist antibodies or antibody fragments, muramyl-dipeptide analogues of muramyl-L-alanine and/or compounds that include muramyl-L-alanine in their core structure, and small organic molecules, etc.

Methods for identifying antagonists of a muramyl-L-alanine and/or compounds that include muramyl-L-alanine in their core structure may comprise contacting a muramyl-L-alanine and/or compounds that include muramyl-L-alanine in their core structure with the LRR domain of CaCdc35p in the presence of a candidate agonist or antagonist molecule and measuring hyphal growth.

Consistent with the invention there are provided (a) antibodies to muramyl-L-alanine and/or compounds that include muramyl-L-alanine in their core structure and (b) antibodies that engage the LRR domain of CaCdc35p preventing muramyl-L-alanine and/or compounds that include muramyl-L-alanine in their core structure from binding to the LRR domain. Exemplary antibodies include polyclonal, monoclonal, humanized, bispecific, and heteroconjugate antibodies.

A. Polyclonal Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant.

Typically, the immunizing agent and/or adjuvant will be injected in the mammal by multiple subcutaneous or intraperitoneal injections. The intensity of the response is determined by several factors including the size of the immunogen molecule, its chemical characteristics, and how different it is from the animal's own proteins. Most natural immunogens are proteins with a molecular weight above 5 kDa that come from sources phylogenically far removed from the host animal (i.e., human proteins injected into rabbits or goats). It is desirable to use highly purified proteins as immunogens, since the animal will produce antibodies to even small amounts of impurities present as well as to the major component. The antibody response increases with repeated exposure to the immunogen, so a series of injections at regular intervals is needed to achieve both high levels of antibody production and antibodies of high affinity.

To the extent that the antagonist is an antibody that engage the LRR domain of CaCdc35p preventing muramyl-L-alanine and/or compounds that include muramyl-L-alanine in their core structure from binding to the LRR domain the immunogen will be an selected from amino acids comprising the LRR domain from CaCdc35p. Preferably, the amino acid sequence will be selected from the region of about 363 to 927 in the CaCdc35p protein. Sequences of at least 5, 6, 7, 8, 9, 10, 15, 20, 25, 30 amino acids from this region will generally be used to generate those antibodies. Desirably, the sequence selected will generate an antibody that specifically interferes with binding of muramyl-L-alanine and/or compounds that include muramyl-L-alanine in their core structure to the LRR domain of only CaCdc35p.

Not all immunogenic molecules will however generate the level of antibody desired. To increase the intensity of the immune response immunogens are combined with complex mixtures called adjuvants. Adjuvants are a mixture of natural or synthetic compounds that, when administered with antigens, enhance the immune response. Adjuvants are used to (1) stimulate an immune response to an antigen that is not inherently immunogenic, (2) increase the intensity of the immune response, (3) preferentially stimulate either a cellular or a humoral response (i.e., protection from disease versus antibody production). Examples of adjuvants which may be employed include Freund's complete adjuvant and MPL-TDM adjuvant (monophosphoryl Lipid A, synthetic trehalose dicorynomycolate). A more extensive discussion of adjuvants and their use in immunization protocols is given in Immunology Methods Manual, vol. 2, I. Lefkovits, ed., Academic Press, San Diego, Calif., 1997, ch. 13. Immunology Methods Manual is available as a four volume set, (Product Code Z37, 435-0); on CD-ROM, (Product Code Z37, 436-9); or both, (Product Code Z37, 437-7)

If the immunogen is still unable to generate an acceptable response, it may be conjugated to a carrier protein that is more immunogenic. Small molecules such as drugs, organic compounds, and peptides and oligosaccharides with a molecular weight of less than 2-5 kDa like, for example, muramyl-L-alanine and/or compounds that include muramyl-L-alanine in their core structure, are not usually immunogenic, even when administered in the presence of adjuvant. In order to generate an immune response to these compounds, it is necessary to attach them to a protein or other compound, termed a carrier that is immunogenic. When attached to a carrier protein the small molecule immunogen is called a hapten. Haptens are also conjugated to carrier proteins for use immunoassays. The carrier protein provides a means of attaching the hapten to a solid support such as a microtiter plate or nitrocellulose membrane. When attached to agarose they may be used for purification of the anti-hapten antibodies. They may also be used to create a multivalent antigen that will be able to form large antigen-antibody complexes. When choosing carrier proteins, remember that the animal will form antibodies to the carrier protein as well as to the attached hapten. It is therefore relevant to select a carrier protein for immunization that is unrelated to proteins that may be found in the assay sample. If haptens are being conjugated for both immunization and assay, the two carrier proteins should be as different as possible. This allows the antiserum to be used without having to isolate the anti-hapten antibodies from the anti-carrier antibodies.

Where the immunizing agent is muramyl-L-alanine and/or compounds that include muramyl-L-alanine in their core structure preferably the muramyl-L-alanine and/or compounds that include muramyl-L-alanine in their core structure are conjugated to a protein known to be immunogenic in the mammal being immunized.

Examples of such immunogenic proteins include but are not limited to keyhole limpet hemocyanin (KLH), serum albumin, bovine thyroglobulin, soybean trypsin inhibitor, and a toxoid, for example tetanus toxoid.

KLH is a respiratory protein found in molluscs. Its large size makes it very immunogenic, and the large number of lysine residues available for conjugation make it very useful as a carrier for haptens. The phylogenic separation between mammals and molluscs increases the immunogenicity and reduces the risk of cross-reactivity between antibodies against the KLH carrier and naturally occurring proteins in mammalian samples.

KLH is offered both in its native form, for conjugation via amines, and succinylated, for conjugation via carboxyl groups. Succinylated KLH may be conjugated to a hapten containing amine groups (such as a peptide) via cross-linking with carbodiimide between the newly introduced carboxyl groups of KLH and the amine groups of the hapten.

Protocols for conjugation of haptens to carrier proteins may be found in *Antibodies: A Laboratory Manual*, E. Harlow and D. Lane, ed., Cold Spring Harbor Laboratory (Cold Spring Harbor, N.Y., 1988) pp. 78-87 (Product Code A 2926)

The immunization protocol may be selected by one skilled in the art without undue experimentation. Protocols for preparing immunogens, immunization of animals, and collection of antiserum may be found in *Antibodies: A Laboratory Manual*, E. Harlow and D. Lane, ed., Cold Spring Harbor Laboratory (Cold Spring Harbor, N.Y., 1988) pp. 55-120 (Product Code A 2926).

B. Monoclonal Antibodies

The antibodies may, alternatively, be monoclonal antibodies. Monoclonal antibodies may be prepared using hybridoma methods, such as those described by Kohler and Milstein (1975), *Nature*, 256:495. In a hybridoma method, a mouse, hamster, or other appropriate host animal, is typically immunized with an immunizing agent as described above to elicit lymphocytes that produce or are capable of producing antibodies that will specifically bind to the immunizing agent. Alternatively, the lymphocytes may be immunized in vitro.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. (1984) Immunol., 133:3001).

The culture medium in which the hybridoma cells are cultured can then be assayed for the presence of monoclonal antibodies directed against muramyl-L-alanine and/or compounds that include muramyl-L-alanine in their core structure.

After the desired hybridoma cells are identified, the clones may be subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

In vitro methods are also suitable for preparing monovalent antibodies. Digestion of antibodies to produce fragments thereof, particularly, Fab fragments, can be accomplished using routine techniques known in the art.

C. Human and Humanized Antibodies

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding sub-sequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., (1986) Nature, 321:522-525; Riechmann et al., (1988) Nature, 332:323-327; Verhoeyen et al., (1988) Science 239:1534-1536], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. (1991) Mol. Biol., 227:381; Marks et al., (1991) J. Mol. Biol., 222:581]. The techniques of Cole et al. and Boerner et al. are also available for the preparation of human monoclonal antibodies (Cole et al., (1985) Monoclonal Antibodies and Cancer Therapy, Alan R. Liss, p. 77 and Boerner et al., (1991) J. Immunol., 147(1):86-95]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., (1992) Bio/Technology 10, 779-783; Lonberg et al., (1994) Nature 368 856-859; Morrison, (1994) Nature 368, 812-13; Fishwild et al., (1996) Nature Biotechnology 14, 845-51; Neuberger, (1996) Nature Biotechnology 14, 826; Lonberg and Huszar, (1995) Intern. Rev. Immunol. 13 65-93.

D. Bispecific Antibodies

Bispecific antibodies are monoclonal, preferably human or humanized, antibodies that have binding specificities for at least two different antigens. In the present case, one of the binding specificities is for muramyl-L-alanine and/or a compound that includes muramyl-L-alanine in its core structure, the other one is for another compound having muramyl-L-alanine in its core structure.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, (1983) Nature, 305:537-539].

E. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

F. Immunoconjugates

The invention also pertains to immunoconjugates comprising an antibody conjugated to a cytotoxic agent such as a chemotherapeutic agent, toxin (e.g., an enzymatically active toxin against *Candida*), or a radioactive isotope (i.e., a radioconjugate).

Conjugates of the antibody and cytotoxic agent are made using a variety of bifunctional protein-coupling agents such as N-succinnimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Compositions of the Invention

Antibodies produced according to the invention, as well as other molecules identified by the screening assays disclosed herein, can be administered for the treatment of *Candida* infection in the form of pharmaceutical compositions.

Thus, the present invention also relates to compositions including pharmaceutical compositions comprising a therapeutically effective amount of an antagonist to muramyl-L-alanine and/or compounds that include muramyl-L-alanine in their core structure. As used herein a compound will be therapeutically effective if it is able to affect *Candida* hyphal growth.

Pharmaceutical forms of the invention suitable for injectable use include sterile aqueous solutions (where water soluble) or dispersions and sterile powders for the extemporaneous preparation of sterile injectable solutions and or one or more carrier. Alternatively, injectable solutions may be delivered encapsulated in liposomes to assist their transport across cell membrane. Alternatively or in addition such preparations may contain constituents of self-assembling pore structures to facilitate transport across the cellular membrane. It must be stable under the conditions of manufacture and storage and must be preserved against the contaminating/destructive action of microorganisms such as, for example, bacteria and fungi.

The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as, for example, lecithin, by the maintenance of the required particle size in the case of dispersion and by the use of surfactants. Preventing the action of microorganisms in the compositions of the invention is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze-drying, to yield a powder of the active ingredient plus any additional desired ingredient from previously sterile-filtered solution thereof.

When the active ingredients, in particular small molecules contemplated within the scope of the invention, are suitably protected they may be orally administered, for example, with an inert diluent or with an edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that a dosage unit form contains between about 0.1 µg and 20 g of active compound.

The tablets, troches, pills, capsules and the like may also contain binding agents, such as, for example, gum, acacia, corn starch or gelatin. They may also contain an excipient, such as, for example, dicalcium phosphate. They may also contain a disintegrating agent such as, for example, corn starch, potato starch, alginic acid and the like. They may also contain a lubricant such as, for example, magnesium stearate. They may also contain a sweetening agent such a sucrose, lactose or saccharin. They may also contain a flavouring agent such as, for example, peppermint, oil of wintergreen, or cherry flavouring.

When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparaben as preservatives, a dye and flavouring such as, for example, cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as, for example, creams, lotions and gels. Such a formulation comprises a gelling agent in a concentration effective to promote gelling upon contact with the eye or with lacrimal fluid in the exterior of the eye. Suitable gelling agents include, but are not limited to, thermosetting polymers such as tetra-substituted ethylene diamine block copolymers of ethylene oxide and propylene oxide (e.g., poloxamine); polycarbophil; and polysaccharides such as gellan, carrageenan (e.g., kappa-carrageenan and iota-carrageenan), chitosan and alginate gums.

To this extent the active ingredient may be held within a matrix which controls the release of the active agent. Preferably, the matrix comprises a substance selected from the group consisting of lipid, polyvinyl alcohol, polyvinyl acetate, polycaprolactone, poly(glycolic)acid, poly(lactic) acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly (ortho esters), sucrose acetate isobutyrate (SAIB), and combinations thereof and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety. Preferably, the matrix sustainedly releases the drug.

Pharmaceutically acceptable carriers and/or diluents may also include any and all solvents, dispersion media, coatings, antibacterials and/or antifungals, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated.

Supplementary active ingredients can also be incorporated into the compositions. Preferably those supplementary active ingredients are antifungal agents such as antifungal antibiotics like, for example, polyenes (e.g., amphotericin b, candicidin, dennostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin). Alternatively they may be synthetic antifungals such as allylamines (e.g., butenafine, naftifine, terbinafine), imidazoles (e.g., bifonazole, butoconazole, chlordantoin, chlormiidazole, cltoconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired therapeutic effect in association with the required pharmaceutical carrier. The dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 pg to about 2000 mg/ml of carrier. In the case of compositions containing supplementary active ingredients, the dosages are determined by reference to the usual dose and manner of administration of the said ingredients.

Prognosing or Diagnosing the Course of a *Candida* Infection

The invention also provides a means for prognosing or diagnosing the course of a *Candida* infection, comprising the steps of: measuring the amount of muramyl-L-alanine and/or compounds that include muramyl-L-alanine in their core structure in body fluids sampled from a *Candida* infection.

Further the invention provides a means for determining the most effective treatment for a *Candida* infection, comprising the steps of: diagnosing the state of hyphal growth according to the above method and then determining the patient's treatment according to whether hyphal growth is expected or not.

Diagnostic and prognostic methods will generally be conducted using a biological sample obtained from a patient. A "sample" refers to a sample of tissue or fluid suspected of containing an muramyl-L-alanine and/or compounds that include muramyl-L-alanine in their core structure from an individual including, but not limited to, e.g., plasma, serum, spinal fluid, lymph fluid, the external sections of the skin, respiratory, intestinal, and genitourinary tracts, tears, saliva, blood cells, tumours, organs, tissue and samples of in vitro cell culture constituents.

According to the diagnostic and prognostic methods of the present invention, alteration of levels of muramyl-L-alanine and/or compounds that include muramyl-L-alanine in their core structure in body fluids may be detected using anyone of the methods described herein.

Alteration of levels of muramyl-L-alanine and/or compounds that include muramyl-L-alanine in their core structure in body fluids can be detected by screening for such compounds. Such alterations can be determined by any assay that detects changes in the level of muramyl-L-alanine and/or compounds that include muramyl-L-alanine in their core structure such as biochemical assays like HLPC assays and the like or immunological assays in accordance with conventional techniques. Antibodies (polyclonal or monoclonal) as described herein may be used to detect muramyl-L-alanine and/or compounds that include muramyl-L-alanine in their core structure in body fluids. The antibodies may be prepared as discussed above. Immunological assays can be done in any convenient format known in the art. These include Western blots, immunohistochemical assays and ELISA assays. Any means for detecting a binding pair can be used. Functional assays, such as protein binding determinations, can be used.

Screening for Agonists and Antagonists of *Candida* Hyphal Growth

Consistent with the invention there is provided a means for screening for agonists and antagonists of *Candida* hyphal growth comprising the steps of: (a) contacting (i) muramyl-L-alanine and/or compounds that include muramyl-L-alanine in their core structure and (ii) the LRR domain of CaCdc35p from a *Candida* species with a sample compound, and (b) detecting whether the sample compound exhibits agonistic or antagonistic activity towards the interaction. Preferably, the method is used to screen for antagonistic drugs that are capable of interfering either in a direct or indirect manner with the interaction between *C. albicans* and muramyl-L-alanine, muramyl-L-alanyl-D-isoglutamine, N-acetyl-muramyl-L-alanine, N-acetyl-muramyl-L-alanyl-D-isoglutamine, or muramyl-L-alanyl-L-isoglutamine.

Screening assays for antagonist drug candidates are designed to identify compounds that bind the LRR domain of CaCdc35p to inhibit the binding of muramyl-L-alanine and/or compounds that include muramyl-L-alanine in their core structure with the protein or interfere with the interaction between muramyl-L-alanine and/or compounds that include muramyl-L-alanine in their core structure and the LRR domain of CaCdc35p. Such screening assays will include assays amenable to high-throughput screening of chemical libraries, making them particularly suitable for identifying small molecule drug candidates.

The assays can be performed in a variety of formats, including protein binding assays, biochemical screening assays, immunoassays, and cell-based assays, which are well characterized in the art. Such assays for antagonists are common in that they call for contacting muramyl-L-alanine and/or compounds that include muramyl-L-alanine in their core structure and the LRR domain of CaCdc35p in the presence of the drug candidate for a time sufficient to allow these components to interact.

Compounds that interfere with the interaction can be tested as follows: usually a reaction mixture is prepared containing muramyl-L-alanine and/or compounds that include muramyl-L-alanine in their core structure and at least the LRR domain of CaCdc35p for a time allowing for the interaction and binding of the products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular components present in the mixture is monitored as described hereinabove. The formation of a complex in the control reaction(s) but not in the reaction mixture containing the test compound indicates that the test compound interferes with the interaction of the test compound and its reaction partner.

Potential antagonists include small molecules that bind to the site in the LRR domains where muramyl-L-alanine and/or compounds that include muramyl-L-alanine in their core structure bind, thereby blocking the normal biological activity of muramyl-L-alanine and/or compounds that include muramyl-L-alanine in their core structure. Examples of small molecules include, but are not limited to, small peptides or peptide-like molecules, preferably soluble peptides, and synthetic non-peptidyl organic or inorganic compounds.

These small molecules can be identified by any one or more of the screening assays discussed hereinabove and/or by any other screening techniques well known for those skilled in the art.

The present invention also relates to compounds identified by the above method and their use in treating *Candida* hyphal growth in a patient.

Non-Limiting Illustration of the Invention

Further features of the present invention are more fully described in the following description. This description is included solely for the purposes of exemplifying the present invention. It should not be understood as a restriction on the broad description of the invention as set out above.

The following discussion describes the identification and functional characterization of the hyphal inducer(s) in human and bovine sera and their sensor in *C. albicans*. It shows that peptidoglycan-like molecules are significantly enriched in the chromatographic fractions of serum with strong hypha-inducing activity. Through chemical synthesis, the inventor has found that compounds with a core structure of muramyl-L-alanine (eg: FIG. 1) are potent hyphal inducers with muramyl-L-alanine-D-isoglutamine being the most active. They also show that the inducers may directly bind the LRR domain of the adenylate cyclase Cdc35, stimulate cAMP production and promote hyphal growth.

Co-Precipitation of Hypha-Inducing Activity from Serum with Serum Proteins

Figure 2:
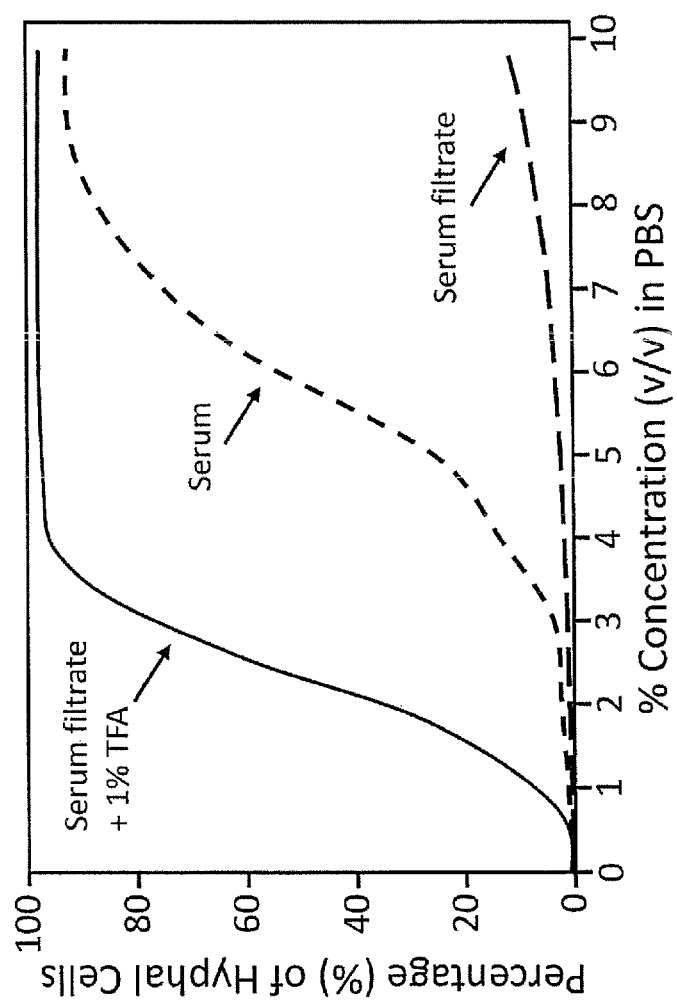
FIG. 2: Shows that 2% of the filtrate of TFA treated serum induced more than 90% of the yeast cells to switch to hyphal growth.
Figure 3:
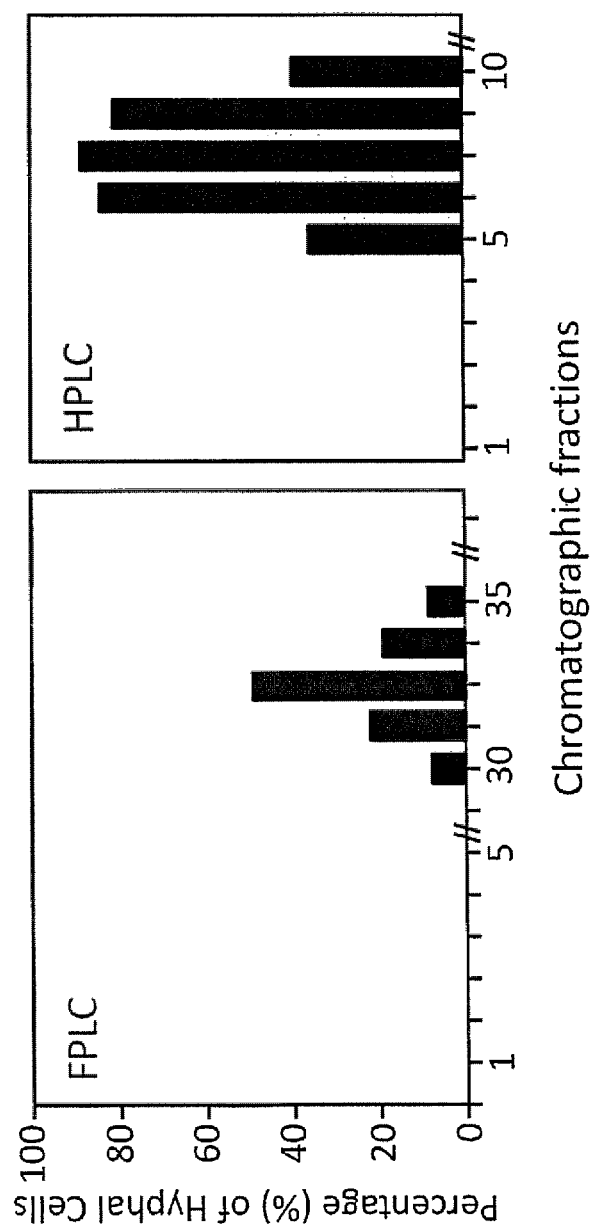
FIG. 3: FPLC and HPLC results of the serum filtrates
Figure 4:
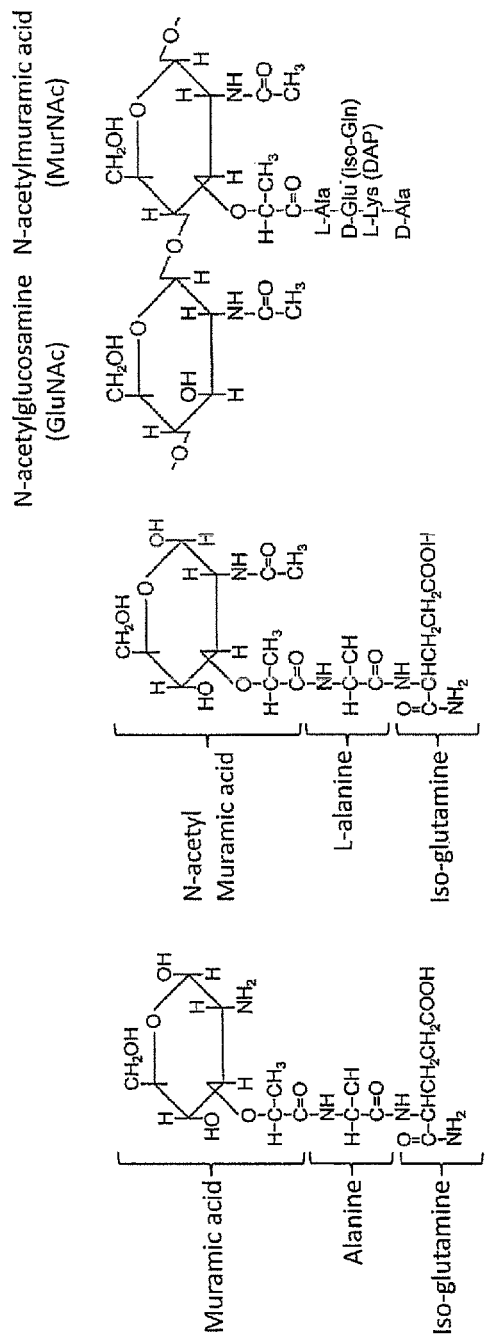
FIG. 4: Structures of muramic-L-alanene isoglutamate (left), muramic dipeptide (MDP) (middle) and a peptogycan subunit (right)
Figure 5:
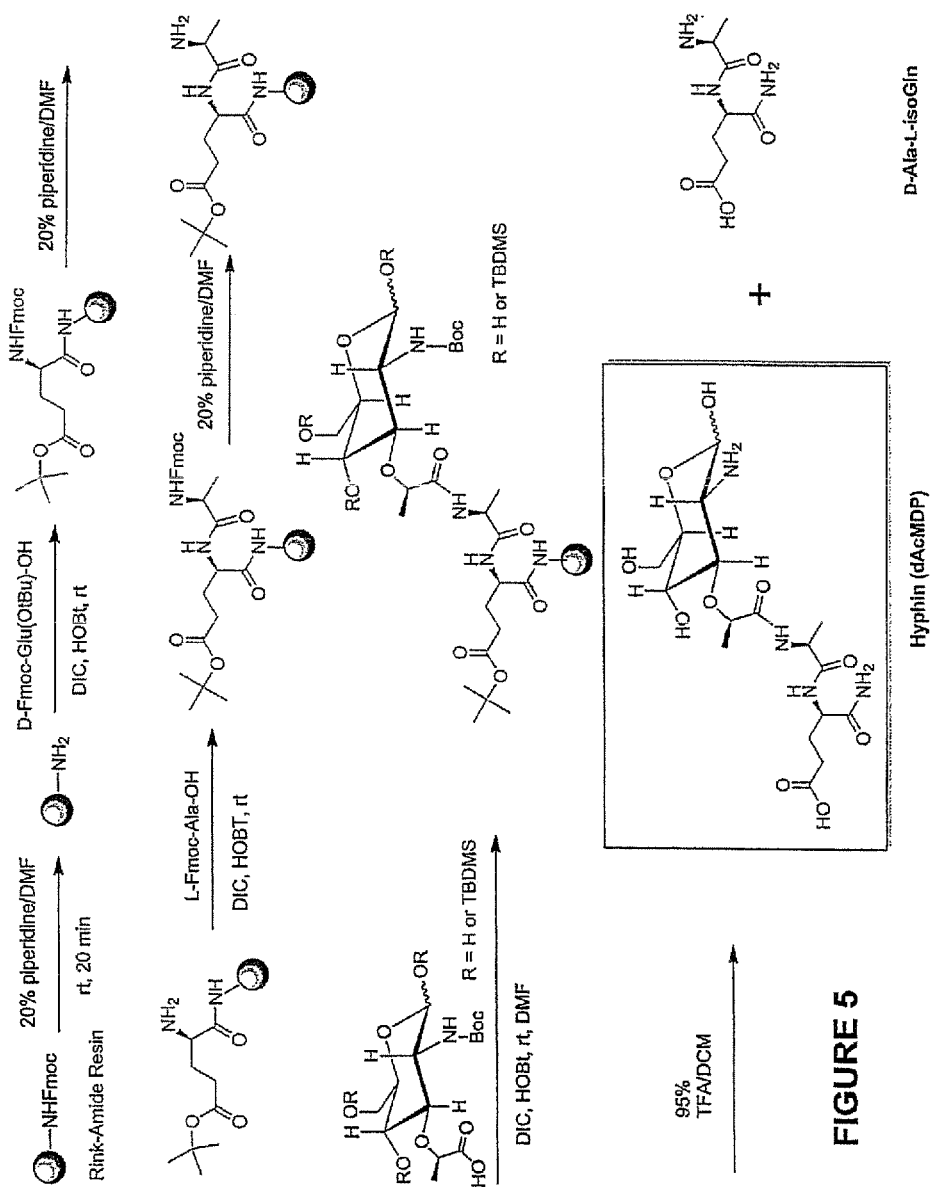
FIG. 5: Solid phase synthesis of hyphin a muramyl-L-alanine that does not have the N-acetyl group commonly found in bacterial PGNs

Precipitation of serum proteins with acetonitrile trapped about ~60-70% of the hypha-inducing activity in the protein pellet and a brief treatment of serum at room temperature with weak acid, such as 1% trifluoroacetic acid (TFA), was sufficient to release a majority of the activity into supernatant (FIG. 2). The results indicate that a majority of the hypha-inducing agents, in serum is present in protein-bound form. Hence, in the fractionation procedure described below the bovine and human sera were first treated with 1% TFA before filtration through a membrane with a molecular weight cut off of 3 kDa to remove serum proteins. Fast performance liquid chromatography (FPLC) fractionation of the serum filtrate detected significant hypha-inducing activity in a single peak centered about fraction 30 (Ff) (FIG. 3, left). Ff30 was highly active in hyphal induction, inducing 50% germ tube formation ($I_{50}$) at ~0.2 mg (dry weight)/ml. In comparison, fresh serum and the <3 kDa filtrate had $I_{50}$ values of ~5.5 and 1.3 mg/ml respectively. Further separation of Ff30 by using conventional reversed-phase high performance liquid chromatography (HPLC) found the hypha-inducing activity to be relatively evenly present in fractions 5 to 10. To achieve better separation, the active fractions 5 to 10 were pooled, freeze-dried and subjected to a. second round of reversed-phase HPLC using a Waters Atalantis dC18, 5 µM column. This column allows the use of aqueous mobile phase and provides much improved retention of polar compounds. The hyphal induction assay located high hypha-inducing activity in fractions with retention times from 10 and 14 min corresponding to a group of peaks with low UV absorption (FIG. 3). The active fractions (Hf 10/14), when pooled, exhibited an $I_{50}$ of approximately 0.12 mg/ml. The hypha-inducing activity of both human and bovine sera exhibited nearly identical chromatographic profiles and retention times, indicating that the inducers are similar in nature. Attempts to further resolve the active fractions by using a range of sizing, ion exchange and affinity chromatography were not successful, because the activity was always distributed rather broadly. Inventor obtained a total of approximately 7 mg of dry material of Hf10/14 from 500 ml serum and subjected it for NMR analysis. The NMR spectra cleared showed signals for glucose, fructose, glycerol and lactic acid. However, none of these compounds was found to have appreciable hypha-inducing activity individually or in combination in PBS or Hank's solution. However, further analysis of the low intensity NMR signals suggested the presence of muramic acid, alanine and isoglutamine. However, owing to the weak signals and impurity of the sample, there was uncertainty whether the three moieties belong to the same molecule. Intriguingly, muramic acid (Mur) is thought to be only present in bacterial PGs in nature; and alanine and isoglutamine are very common amino acids of the short peptides cross-linking the N-acetylglucosamine-N-acetylmutamic acid chains in PGs (FIG. 1). Thus, two chemical structures have been identified: muramyl-L-alanine (FIG. 1 top) and muramyl-L-alanyl-D-isoglutamine (FIG. 1 bottom and FIG. 4). Inventor also noted that in nature muramic acid is almost universally found in 2-N-acetyl form, but their NMR data did not detect this group in the proposed muramic acid.

The Presences of Mur-Containing Compounds in the Active Serum Fractions

Although Mur-containing compounds have been detected in a range of normal and inflammatory tissues of mammals (including brain, kidney, liver and peripheral leukocytes and in urine), its presence in serum remains controversial.

Established protocols were used to confirm the presence of Mur-containing molecules in serum and their enrichment in the chromatographic fractions active for hyphal induction. To release free Mur, samples were first hydrolyzed with 4N HCl and then reduced by sodium borohydride to remove the anomeric center of the ring that is well known to cause the splitting of chromatographic peaks. To enhance detection sensitivity, the reduced samples were derivatized by dansylation, which adds a fluorescent dansyl group to each free $NH_2$ group. The dansylated samples were separated by reversed-phase HPLC using a Waters Sunfire C18 column. The UV spectra of Hf10/14 processed by following the above protocol showed a well isolated peak with a retention time of 22.07 min that matches that of the authentic Mur processed in an identical fashion (FIG. 3). Mass spectrometry (MS) analysis of this peak of the derivatized authentic Mur revealed a clean spectrum with two prominent ions of m/z 487.1 $(M+H)^+$ and 469.1 that are consistent with dansyl Mur and dansyl Mur minus one $H_2O$ respectively. MS analysis of the peak from Hf10/14 produced both 487.1 and 469.1 ions. To gain more robust results borohydride was replaced with sodium borodeuteride in the reduction step, which is expected to increase the mass of the dansylated Mur to 488.1. Under this condition, HPLC detected the same peak at 22.07 min and MS analysis of the peak revealed strong ions of m/z 488.1 and 470.1. By contrast, the Mur signals were not detected if the HCl hydrolysis step was omitted; indicating that serum Mur is predominantly present as a moiety of larger PG fragments. Furthermore, significant Mur signals were not detected from any of the serum fractions without hypha-inducing activity, indicating that the majority of serum Mur-containing compounds are concentrated in the chromatographic fractions with strong hypha-inducing activity. Using this protocol Mur was invariably detected from several different batches of bovine sera, 2 human plasma samples and 10 human sera. Mur was not detected from mock samples (water or PBS) processed by following the same procedure, excluding the possibility of bacterial contamination. When the <3 kDa serum filtrate was directly processed by this protocol, the HPLC peak for dansyl Mur overlapped with high chemical complexity of the filtrate, made the detection difficult. This observation might explain, at least in part, why some earlier efforts failed to detect Mur in serum. In summary, the NMR data suggested the presence of muramyl-L-alanyl-D-isoglutamine in the serum fractions enriched for hypha-inducing activity; and subsequently MS analysis confirmed a significant enrichment of Mur-containing molecules and detected a MS ion corresponding to the mass of muramyl-alanyl-isoglutamine in the same fractions. This is believed to be the first unequivocal detection of Mur-containing molecules in sera from healthy people and animals. Using authentic muramic acid as a standard in HPLC, the total amount of muramic acid detected in the FPLC fractions Hf31 to 33 was quantified. These data established that the amount of Mur in both human and bovine serum is at least 0.5-1 mM.

Synthetic PG Components Exhibited Potent Hypha-Inducing Activity

To determine whether the NMR-elucidated compound is active for hyphal induction, solid-phase chemical synthesis was undertaken of muramyl-L-alanyl-D-isoglutamine (MLADiQ) and muramyl-L-alanine (MLA). N-acetylmuramyl-L-alanyl-D isoglutamine (NMLADiQ) and N-acetyl-murmyl-L-alanine (NMLA) was also synthesized together with compounds containing D-alanine (MDA and MDADiQ) and L-isoglutamine (MLALiQ) to evaluate the, importance of the N-acetyl group and the stereo-chemical configuration of the amino acids for hyphal induction. The schemes for chemical synthesis of the compounds followed standard procedures. All the synthesized compounds were purified by HPLC and their identities confirmed by MS. The $I_{50}$ of each compound was then determined. These data revealed that MLADiQ was a highly potent hyphal inducer with an $I_{50}$ of approximately 10 μM. Strikingly, the N-acetylated compound NMLADiQ had an $I_{50}$ of approximately 6 mM, 600 times less active than MLADiQ. Also, NMLADiQ at increased concentrations was never able to induce higher than 60% germ tube formation and the activity started to drop significantly when the concentration was raised above 20 mM. MLA was also active with an $I_{50}$ of approximately 200 μM, while NMLA had an $I_{50}$ of approximately 8 mM and exhibited similar diminishing hypha-inducing activity at high concentrations as NMLADiQ. The compounds with the L-alanine substituted by D-alanine (MDA and MDADiQ) were inactive for hyphal induction, whereas the compound with the D-isoglutamine replaced by L-isoglutamine (MLA-LiQ) exhibited reduced but still substantial activity with an $I_{50}$ of approximately 180 μM. Neither muramic nor N-acetyl-muramic acid was active for hyphal induction. N-Acetylglucosamine (NAG), the strongest single-compound hyphal inducer previously known had an $I_{50}$ of approximately 3 mM. Glucose had no activity in the assay conditions. Taken together, the following conclusions can be drawn from these data. First, MLADiQ is a highly potent hyphal inducer, consistent with the NMR-elucidated chemical structure. Second, the absence of the, N-acetyl group in the muramyl moiety is crucial for high hypha-inducing activity, which provides an excellent explanation about why our NMR' analysis did not detect signals for the N-acetyl group. Hyphin of FIG. 1 does not have the N-acetyl group commonly found in bacterial PGNs. Third, muramyl-L-alanine appears to be the minimal structure required and its L configuration is essential for the hypha-inducing activity. Fourth, the results suggest that other PG components structurally related to MLADiQ may also be active for hyphal induction.

The Role of the LRR Domain of *C. Albicans* Adenylate Cyclase CaCdc35p

Pathogen-associated molecular patterns, including PG motifs, are known to be recognized by LRR domain-containing proteins in mammals, plants and *Drosophila* to initiate host innate immune response. In view of these data studies were carried out to determine if *C. albicans* might use a similar mechanism for MLADiQ sensing.

BLAST-searches were conducted to on the *C. albicans* genome database to identify proteins that may contain LRR domain-containing proteins. Data from these searches lead to the identification of a single significant match with CaCdc35p. CaCdc35p is a large protein of 1690 amino acids (aa) with multiple functional domains: a Ras association (RA) domain (aa 304-393), 15 LRRs (aa 490-927) organized in three clusters, and an adenylyl cyclase (CYCc) domain (aa 12471500). CaCdc35p has been positioned near the top of the cAMPIPKA signal transduction pathways for hyphal growth (Leberer, E., et al. (2001) Mol. Microbiol. 42, 673-687; Roche, C. R., et al (2001) Mol. Biol. Cell 12, 3631-3643). CaCDC35 deletion mutant is completely blocked for hyphal development and exhibits severely retarded yeast growth as well (Leberer, E., et al. (2001) Mol. Microbiol. 42, 673-687). To assess whether CaCdc35p LRR domain is required for sensing MLADiQ, a series of cacdc35 mutants deleted of either the entire LRR domain (IrrΔ) or each of the three LRR clusters (Irr1Δ, Irr2Δ and Irr3Δ) were created. Point mutations were also introduced in some of the highly conserved residues within a repeat. For example, mutants Irr5mu and Irr9mu carrying Leu→Ala and Asn→Ala mutations in repeats 5, and 9 respectively. The genomic DNA fragment encoding CaCdc35p and approximately 500 bp of both 5' and 3' flanking sequences was cloned in plasmid Clp10 as the template for mutation. Each of the constructs was integrated at a specific site in the promoter region of the CaCDC35 locus in a cacdc35A mutant and the expression was verified by Western blot analysis. The wild-type CaCDC35 fully rescued the hyphal development defect of cacdc35Δ in response to MLADiQ as well as serum and reduced the doubling time of yeast growth from 4.46 h to 1.67 h in GMM at 30° C. Strikingly, although all LRR domain mutants largely rescued the retarded yeast growth of cacdc35Δ, none restored to any extent the hyphal development in response to MLADiQ and serum. The results suggest that the LRR domain may have a specific role in mediating the hypha-inducing signals and this activity is largely separable from the general growth function of the protein.

One crucial early event in C. albicans hyphal growth is the occurrence of a spike of intracellular cAMP. The observation that the LRR domain mutants rescued the yeast growth defect of cacdc35A but not the hyphal growth defect suggests that the mutated CaCdc35p may be able to provide a basal level of cellular cAMP which is important for general growth functions but unable to increase cAMP production which is required for the activation of the cAMP/PKA pathway. To test this hypothesis, cAMP levels were examined in wild-type and several LRR domain mutants in response to MLADiQ treatment. The yeast cells were treated with 50 μM MLADiQ, a concentration that consistently induced near 100% yeast-hypha switch in wild-type strains, and aliquots were harvested every 20 min for cAMP assay. In the wild-type yeast cells the intracellular cAMP level was found to be approximately 1.7 pmol/mg dry cells. Upon hyphal induction by MLADiQ at 37° C. the cAMP level rapidly rose to 3.8 by 30 to 40 min, gradually declined in the next 30 min to approximately 2.8 pmol and remained at this level during hyphal growth. By contrast, cAMP was undetectable in cacdc35Δ cells. Re-introducing in the mutant a copy of CaCDC35, IrrΔ or Irr9mu restored the CAMP level to 1.2-1.7 pmol/mg dry cells during yeast growth. However, the MLADiQ-induced cAMP spike was only detected in the cacdc35Δ cells transformed with CaCDC35. The results demonstrate that the LRR domain mutants can provide a basal level of cellular cAMP but unable to increase it in response to MLADiQ treatment.

Next, assays were performed for the conversion of $\alpha$-$^{32}$P-ATP to $\alpha$-$^{32}$P-cAMP in cell lysate after the addition of MLADiQ, which is a direct measure of the adenylate cyclase activity. Cell lysate was prepared by glass bead-beating of cells under non-denaturing conditions. Adding MLADiQ to the wild-type lysate activated a32P-cAMP production and as low as approximately 6 μM of MLADiQ was sufficient to induce the maximum level of activation of the catalytic activity. By contrast, no increase of the cyclase activity was observed in the lysates of IrrΔ and Irr9mu cells. The data indicate that MLADiQ directly enhances the adenylate cyclase activity of CaCdc35p in an LRR domain-dependent manner.

Direct Interaction Between Recombinant CaCdc35p LRR Domain and MLADiQ

Next, the possibility that MLA 71Q may directly bind to the LRR domain of CaCdc35p was explored. The wild-type LRR domain and that of Irr9mu were expressed in E. coli as glutathione-S-transferase (GST) fusions and purified to high homogeneity. Then circular dichroism (CD) spectroscopy was used to detect possible direct interaction between the LRR domain and MLADIQ. CD is a reliable tool in detecting conformational changes in a protein as a result of ligand binding (Woody, R. W. (1995). Methods Enzymol. 246, 34-71). Adding MLADiQ to the GST-LRR fusion protein resulted in a significant concentration-dependent shift of the ellipticity values of the CD spectra, whereas this effect was not observed on the spectra of GST-Irr9mu and GST. None of the compounds lacking the hypha-inducing activity exhibited significant effect on the CD spectra of LRR, whereas the less active hyphal inducers MLA, NMLADiQ and NAG caused a weaker but consistent spectrum shift. Together, the results of both the fluorescence and CD spectroscopy demonstrate a direct interaction between MLADiQ and the LRR domain of CaCdc35p as well as an excellent correlation between the hypha-inducing activity of the components and their affinity for LRR binding.

Since specific binding of a molecule to a tryptophan-containing protein may cause concentration-dependent quenching; of tryptophan fluorescence, fluorescence spectroscopy was used to measure the intensity of tryptophan fluorescence of the recombinant LRR domains in the presence of different concentrations of MLADiQ. The results showed that MLADiQ caused significant fluorescence quenching of the GST-LRR fusion in a concentration dependent fashion. In comparison, MDADiQ did not cause any considerable quenching, whereas the less potent inducers MLA, NMLADiQ and NAG induced lower levels of fluorescence quenching. The fluorescence spectrum of GST-Irr9mu appeared similar to that of GST-LRR in the absence of ligand, suggesting that the point mutations had little effect on the overall conformation of the domain. However, the mutated domain did not exhibit detectable fluorescence quenching when mixed with MLADIQ. The fluorescence spectrum of GST was not affected by any of the compounds used. Non-linear regression analysis of the fluorescence quenching as a function of MLADiQ concentration suggested unimodal binding with an equilibrium dissociation constant ($K_d$) of 1.44±0.14 μM and a 1:1 ligand/receptor interaction. MLA, NMLADiQ and NAG exhibited $K_d$ values of 1.67±0.13, 5.26±0.47 and 6.80±0.32 μM respectively.

Modifications of the above-described modes of carrying out the various embodiments of this invention will be apparent to those skilled in the art based on the above teachings related to the disclosed invention. The above embodiments of the invention are merely exemplary and should not be construed to be in any way limiting.

The invention claimed is:

1. A method of determining the extent of Candida hyphal growth in a body fluid sample obtained from a patient having a *Candida* infection, comprising the step of measuring the amount of muramyl-L-alanine and/or compounds that include muramyl-L-alanine in their core structure in the body fluid sample.

2. The method of claim 1, further comprising the step of determining a treatment for the patient according to whether hyphal growth is expected or not.

3. The method of claim 1, wherein the body fluid is selected from the group consisting of: plasma, serum, spinal fluid, lymph fluid, tears and saliva.

4. The method of claim 1, wherein the step of measuring comprises performing a biochemical assay or an immunological assay that detects changes in levels of muramyl-L-alanine and/or compounds that include muramyl-L-alanine in their core structure.

* * * * *